United States Patent
Yoon

(10) Patent No.: US 11,298,389 B2
(45) Date of Patent: Apr. 12, 2022

(54) METHOD FOR PREPARING NON-TOXIC LACQUER, FERMENTED RICE BRAN POWDER USING SAME, AND METHOD FOR MANUFACTURING POWDERED GRAIN NUTRIENT FOOD

(71) Applicant: Hunam Yoon, Uijeongbu-si (KR)

(72) Inventor: Hunam Yoon, Uijeongbu-si (KR)

( * ) Notice: Subject to any disclaimer, the term of this patent is extended or adjusted under 35 U.S.C. 154(b) by 568 days.

(21) Appl. No.: 16/340,311

(22) PCT Filed: Oct. 7, 2016

(86) PCT No.: PCT/KR2016/011259
§ 371 (c)(1),
(2) Date: Jul. 2, 2019

(87) PCT Pub. No.: WO2018/066738
PCT Pub. Date: Apr. 12, 2018

(65) Prior Publication Data
US 2019/0314434 A1    Oct. 17, 2019

(51) Int. Cl.
*A61K 36/22* (2006.01)
*A23L 33/105* (2016.01)
*A23L 5/20* (2016.01)
*C12P 1/00* (2006.01)

(52) U.S. Cl.
CPC ............... *A61K 36/22* (2013.01); *C12P 1/00* (2013.01); *A61K 2236/19* (2013.01)

(58) Field of Classification Search
CPC .......... A23L 33/105; A23L 7/104; A23L 5/20; A23L 3/3472; A23L 7/10; A61K 36/22; A61K 2236/19; C12P 19/22; C12P 1/00
See application file for complete search history.

(56) References Cited

U.S. PATENT DOCUMENTS

2012/0208230 A1* 8/2012 Ha .................................. 435/42

FOREIGN PATENT DOCUMENTS

| KR | 2001-0111159 A | 12/2001 |
|---|---|---|
| KR | 10-0899285 B1 | 5/2009 |
| KR | 10-1071173 B1 | 10/2011 |
| KR | 10-1219650 B1 | 1/2013 |
| KR | 10-1312490 B1 | 10/2013 |
| KR | 10-2016-0081042 A | 7/2016 |

* cited by examiner

*Primary Examiner* — Satyendra K Singh
(74) *Attorney, Agent, or Firm* — Novick, Kim & Lee, PLLC; Jae Youn Kim

(57) ABSTRACT

The present invention provides a method for preparing non-toxic lacquer by detoxifying stems or sprouts of lacquer trees using a malt juice and a fermented rice bran, and a method for manufacturing a fermented rice bran enzyme with improved preservability or a powdered grain nutrient food with improved preservability and dietary property by using the non-toxic lacquer prepared thereby.

6 Claims, 4 Drawing Sheets

Preparing finely cut stems of lacquer trees (S1-1)

Preparing malt liquid (S1-2)

Preparing malt juice (S1-3)

Preparing non-toxic lacquer (S1-4)

Filtering out non-toxic lacquer (S1-5)

METHOD FOR PREPARING NON-TOXIC LACQUER, FERMENTED RICE BRAN POWDER USING SAME, AND METHOD FOR MANUFACTURING POWDERED GRAIN NUTRIENT FOOD

BACKGROUND OF THE INVENTION

Field of the Invention

The present invention relates to a method for preparing non-toxic lacquer by detoxifying stems or sprouts of lacquer trees using a malt juice and a fermented rice bran; and a method for manufacturing a fermented rice bran with improved preservability or a powdered grain nutrient food with improved preservability and dietary properties by using the non-toxic lacquer prepared thereby.

Description of the Related Art

Generally, lacquer means sap coming from liquid trees when trees belonging to Anacardiaceae were hurt. In the Anacardiaceae, there are 60 genera and 400 species of tress found in subtropical regions or tropical regions, and from among these, 5 species such as lacquer trees, Bristly fruit sumac, *Rhus javanica* Linne and so forth, live in Korea.

This lacquer has been used as paints for coating of metal or woodwork and a natural preservative in Korea, China, Japan and so forth, for a long time, and also, since this lacquer has an effect of promoting circulation of human energy and blood and a tonic effect, and produces an effect on menses, a cough and so forth, it also has been used as medicinal ingredients.

However, in the case of direct intake of the lacquer having various medical effects like this in a liquid state (unrefined sap), it has bad side effects such as a rash, pruritus and the like, from a toxic substance called urushiol.

In order to utilize pharmaceutical and biological activity of lacquer, a refining process of roasting the lacquer at a high temperature or carbonizing the lacquer at a high temperature of 200° C. or more in a closed kiln is used by means of a method of neutralizing toxicity of urushiol, but such a process destroys urushiol which is a main ingredient of the pharmaceutical activity as well as an allergenic component of the lacquer, and simultaneously causes a result of removing 100 natural pharmaceutical ingredients contained in the lacquer.

Accordingly, a method for detoxifying the lacquer while not removing the pharmaceutical ingredients of the lacquer has been eagerly required.

PRIOR ARTS

Patent Documents (Patent Document 1) Korean Laid-open Patent Publication No. 2001-0111159 (Title of Invention: ALLERGEN-REMOVED-EXTRACT OF RUSH VERNICIFLUA) describes a method for detoxifying lacquer using a refining process of roasting lacquer at a high temperature or carbonizing the lacquer at a high temperature. However, this method is to remove the pharmaceutical ingredients of the lacquer, simultaneously with detoxifying the lacquer, which is different from the method for preparing non-toxic lacquer in accordance with the present invention capable of preserving the pharmaceutical ingredients of the lacquer, simultaneously with detoxifying the lacquer using a nature-friendly method.

(Patent Document 2), In addition, Korean Patent No. 1219650 (Title of Invention: PROCESS FOR DETOXIFICATION OF RHUS VERNICIFLUA, AND THE USE OF DETOXIFIED BARK EXTRACT) describes a method for detoxifying lacquer using a strain of mushroom and grains, but this method is limited to only mushroom cultivation. Thus, this method is different from the method for preparing non-toxic lacquer in accordance with the present invention which can be used for a variety of ways such as beverage, a fermented rice bran, powder made of dried grains and so forth.

SUMMARY OF THE INVENTION

The present invention is to provide a method for preparing non-toxic lacquer that can detoxify lacquer using a nature-friendly method without any high treatment and can preserve pharmaceutical ingredients of the lacquer entirely by solving the above-described problem, and a method for manufacturing food using the non-toxic lacquer prepared thereby.

In accordance with an aspect of the present invention, a method for preparing non-toxic lacquer using stems of lacquer comprises: cutting stems of lacquer trees in 4 cm to 6 cm lengths and cleaning and drying a same to prepare the cut stems of the lacquer trees; preparing a malt liquid in which malt brews by putting the malt in drinking water for 10 hours or more; putting and sealing the prepared malt liquid and a fermented rice bran in a container and thereafter fermenting them at a temperature in the range of 20° C. to 25° C. for 70 hours or more to prepare a fermented malt juice; and putting and sealing the cut stems of the lacquer trees, the drinking water and the fermented malt juice in the container and thereafter ripening them at a temperature in the range of 10° C. to 25° C. for 5 months or more to prepare the non-toxic lacquer.

In accordance with an aspect of the present invention, the method for preparing the non-toxic lacquer using branches and sprouts of the lacquer trees comprises: cleaning and drying the branches and the sprouts of the lacquer trees and cutting them in 1 cm to 2 cm lengths to prepare the finely cut branches or sprouts of the lacquer trees; preparing a fermented rice bran; and mixing the finely cut branches or sprouts of the lacquer trees, the fermented rice bran and sugar to put and seal them in a pottery and thereafter ripening them at a temperature in the range of 15° C. to 20° C. for 3 months or more, thereby preparing the non-toxic lacquer.

A method for preparing a fermented rice bran powder using the prepared non-toxic lacquer in accordance with another aspect of the present invention comprises: preparing a malt liquid in which malt brews by putting the malt in drinking water for 10 hours or more; forming dough by mixing a polished rice bran (米糠) powder, a malt liquid and the prepared non-toxic lacquer in accordance with an aspect of the present invention; putting the formed dough in a plastic bag and thinly stretching and sealing the formed dough and thereafter fermenting a same at a temperature in the range of 40° C. to 45° C. for 4 days or more, thereby preparing a fermented rice bran; and drying the fermented rice bran at 45° C. or less and thereafter grinding a same to prepare the fermented rice bran powder.

A method for manufacturing a powdered grain food using the prepared non-toxic lacquer in accordance with another aspect of the present invention comprises: immersing or wet-spraying one of grains consisting of rice, barley, barn grass, beans, millet and adlay using drinking water in which the prepared non-toxic lacquer in accordance with an aspect of the present invention is contained at a content of 0.2 wt % to 0.5 wt %, thereby germinating the grains; preparing a malt liquid in which malt brews by putting the malt in the drinking water for 10 hours or more; preparing dried leafy vegetable powder by drying and grinding any one of vegetables, fruits, marine algae, beans or mushrooms; preparing raw green vegetable juice by grinding raw vegetables; forming dough by mixing the germinated grains, the malt liquid, the dried leafy vegetable powder, the fermented rice bran, the raw green vegetable juice and the prepared lacquer in accordance with any one of claims 1 to 4; putting the formed dough in the plastic bag and thinly stretching and sealing the formed dough and thereafter fermenting a same at a temperature in the range of 40° C. to 45° C. for 4 days or more, thereby preparing fermented grains; and drying the fermented grains at 40° C. or less and thereafter grinding a same to prepare the powdered grain food.

In accordance with an aspect of the present invention, a method for preparing non-toxic lacquer which can easily detoxify live branches and/or stems of mature lacquer tress as well as tender sprouts of lacquer trees can be provided.

In addition, according to an aspect of the present invention, the method for preparing non-toxic lacquer which can detoxify lacquer using a nature-friendly method without any high treatment and can entirely preserve pharmaceutical ingredients of the lacquer can be provided.

Meanwhile, in accordance with another aspect of the present invention, the fermented rice bran with excellent enzyme activity and improved preservability using the prepared non-toxic lacquer in accordance with an aspect of the present invention can be provided.

In addition, in accordance with another aspect of the present invention, a powdered grain nutrient food with easy digestion and improved storage using the prepared non-toxic lacquer in accordance with an aspect of the present invention can be provided.

DETAILED DESCRIPTION OF THE PREFERRED EMBODIMENTS

While example embodiments of the present invention are susceptible to various modifications and alternative forms, specific embodiments thereof will be described in detail. It should be understood, however, that there is no intent to limit example embodiments of the invention to the particular forms disclosed, but conversely, example embodiments of the invention are to cover all modifications, equivalents, and alternatives falling within the spirit and scope of the invention. In explanation of the present invention, detailed description of the related art may be omitted when it is considered to unnecessarily obscure the point of the present invention.

The terminology used herein is for the purpose of describing particular embodiments only and is not intended to be limiting of example embodiments of the invention. As used herein, the singular forms "a", "an" and "the" are intended to include the plural forms as well, unless the context clearly indicates otherwise. It should be further understood that the terms "comprises", "comprising,", "includes", "including", and/or "have/has/having", when used herein, specify the presence of stated features, integers, steps, operations, elements, components or groups thereof, but do not preclude the presence or addition of one or more other features, integers, steps, operations, elements, components, or groups thereof.

While terms including ordinal numbers such as "first" and "second" may be used to describe various components, such components are not limited to the terms. The terms are used only for the purpose of distinguishing one component from other components.

The present invention has been devised to provide a method for preparing non-toxic lacquer that can detoxify lacquer using a nature-friendly method without any high treatment and can entirely preserve pharmaceutical ingredients of the lacquer, and a method for manufacturing a variety of foods such as a fermented rice bran, powder made of dried grains, and a grain nutrient food using the non-toxic lacquer prepared thereby.

In the method for preparing non-toxic lacquer according to an aspect of the present invention, detailed steps vary in accordance with the case of using stems or branches (hereinafter referred to as "stems" of lacquer trees) of thick and rough lacquer trees in which lacquer sap comes from its cross section and the case of using thin and tender sprouts of lacquer trees in which pharmaceutical materials of the lacquer are contained but a large amount of lacquer sap does not come from its cross section unlike the case of the thick and rough lacquer trees. However, the detailed steps share the technical feature that the fermented rice bran is used in the detoxifying process.

Figure 1:
FIG. 1 is a stage flowchart of a method for preparing non-toxic lacquer using stems of lacquer trees in accordance with an aspect of the present invention.
Figure 1:
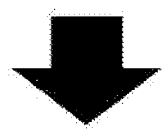
Figure 1:
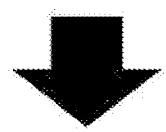
Figure 1:

FIG. 1 is a stage flowchart of a method for preparing non-toxic lacquer using stems (or branches) of lacquer trees in accordance with an aspect of the present invention.

The method for preparing non-toxic lacquer using stems of lacquer trees in accordance with an aspect of the present invention comprises: cutting the stems of the lacquer trees in 4 cm to 6 cm lengths and cleaning and drying a same to prepare the cut stems of the lacquer trees (S1-1); preparing a malt liquid in which malt brews by putting the malt in drinking water for more 10 hours (S1-2); putting and sealing the prepared malt liquid and a fermented rice bran in the pottery and thereafter fermenting them at a temperature in the range of 20° C. to 25° C. for 70 hours or more to prepare a fermented malt juice (S1-3); and putting and sealing the cut stems of the lacquer trees, the drinking water and the fermented malt juice in the container and thereafter ripening them at a temperature in the range of 10° C. to 20° C. for 5 months or more to prepare the non-toxic lacquer (S1-4).

Firstly, the step of preparing the cut stems of the lacquer trees (S1-1) is a process of cutting and cleaning the stems and the branches of the thick and rough lacquer trees in 4 cm to 6 cm lengths to remove foreign objects therefrom and preparing the stems of the lacquer trees dried to the extent of removing moisture.

Next, the step of preparing the malt liquid (S1-2) is a process of preparing the malt liquid by putting malt for more 10 hours, preferably, for 10 to 13 hours, such that water-soluble constituents of the malt are sufficiently dissolved in drinking water.

At this time, the malt is made by forcing and drying sprouts of barley and then milling them, and the malt serves as inducing a diastasic action in starchiness such as grains because it has a large number of amylase as a diastatic enzyme For example, the step is a process that 100 parts by weight of the malt is put in 1700 parts by weight of the drinking water and the malt brews for 10 to 13 hours at room temperature (15° C. to 25° C.), and the step may further comprise a process of filtering out impurities such as barley hulls.

Next, the step of preparing the fermented malt juice (S1-3) is a process that after the malt liquid and the fermented rice bran prepared in the step (S1-2) are put in a porous ceramic container such as a pottery and its opening is covered and sealed by a cotton cloth and the like, they are stored at a temperature in the range of 20° C. to 25° C. for 70 hours or more, preferably, for 70 to 80 hours, thereby preparing the fermented malt juice.

For suscitation of the malt liquid, it is preferable to mix 20 to 30 parts by weight of the fermented rice bran with regard to 100 parts by weight of the prepared malt liquid. This results in the problem that when using less than 20 parts by weight of the fermented rice bran, the suscitation of the malt liquid is inadequate, and when using more than 30 parts by weight thereof, the suscitation of the malt liquid does not last long.

The fermented rice bran used in the step (S1-3) of the method for preparing the non-toxic lacquer in accordance with an aspect of the present invention can be regarded as live enzyme powder made by fermenting, drying and grinding the dough formed by mixing the malt liquid with powder of polished rice bran 米糠 This is a byproduct created after brown rice is polished to white rice and is called rice bran).

It is preferable to utilize the fermented rice bran prepared by further mixing the prepared non-toxic lacquer in accordance with an aspect of the present invention so as to improve activity and a retention period of the fermented rice bran.

If the malt liquid is fermented due to a reaction of a coenzyme of the fermented rice bran, a fermented malt juice with a more reinforced diastasic action of amylase can be obtained.

Lastly, the step (S1-4) of preparing the non-toxic lacquer is a process that the cut stems of the lacquer trees, the drinking water and the fermented malt juice are put in, for example, the pottery and are pressed by heavy stones for press and its opening is then covered and sealed by the cotton cloth and the like, and thereafter, they are fermented and ripened at a temperature in the range of 10° C. to 20° C. for a long period (5 months or more), thereby obtaining the non-toxic lacquer.

For the reaction of detoxification of the lacquer, the mixing at the rate of 100 to 120 parts by weight of the drinking water and 40 to 50 parts by weight of the fermented malt juice, with regard to 100 parts by weight of the cut stems of the lacquer trees, is preferable. This results in the problem that when using the fermented malt juice at a content of less than 40 parts by weight, detoxification of the lacquer is weakened, and when using it at a content of more than 50 parts by weight, an amount of the other natural pharmaceutical ingredients is reduced.

Because a limited inflow of oxygen is needed for proceeding with a smooth detoxification reaction, it is preferable to cover and seal the opening of the container using the cotton cloth and the like.

A ripening temperature is preferably from 10° C. to 20° C., and if it is less than 10° C., the fermentation is weakened to make it difficult to proceed with detoxification, and if it is more than 20° C., the fermentation velocity is excessive, such that toxicity may be left locally.

Additionally, by implementing the step (S1-5) of filtering out the fermented lacquer using the cotton cloth or gauze, pure non-toxic lacquer from which impurities of stems and the like of lacquer trees are removed can be obtained. The non-toxic lacquer from which the impurities are removed is diluted with the drinking water and thus, the non-toxic lacquer diluted with the drinking water can be conveniently drunk.

The lacquer sap (unrefined sap) comes from the finely cut stems of the lacquer trees, but this sap consists of urushiol of 60 to 80%, known as a mixture of divalence phenol, moisture of 10 to 30%, rubber of 7 to 8%, and 100 other natural pharmaceutical ingredients (fucidin, sulurretin, etc.).

In accordance with the method for preparing the non-toxic lacquer according to an aspect of the present invention, as indicated in experimental examples that will be described hereafter, it is assumed that only toxicity of urushiol is selectively removed by enzyme contained in the fermented rice bran as fermented, which can be disproved because a skin rash, pain or the like is not reported.

Figure 2:
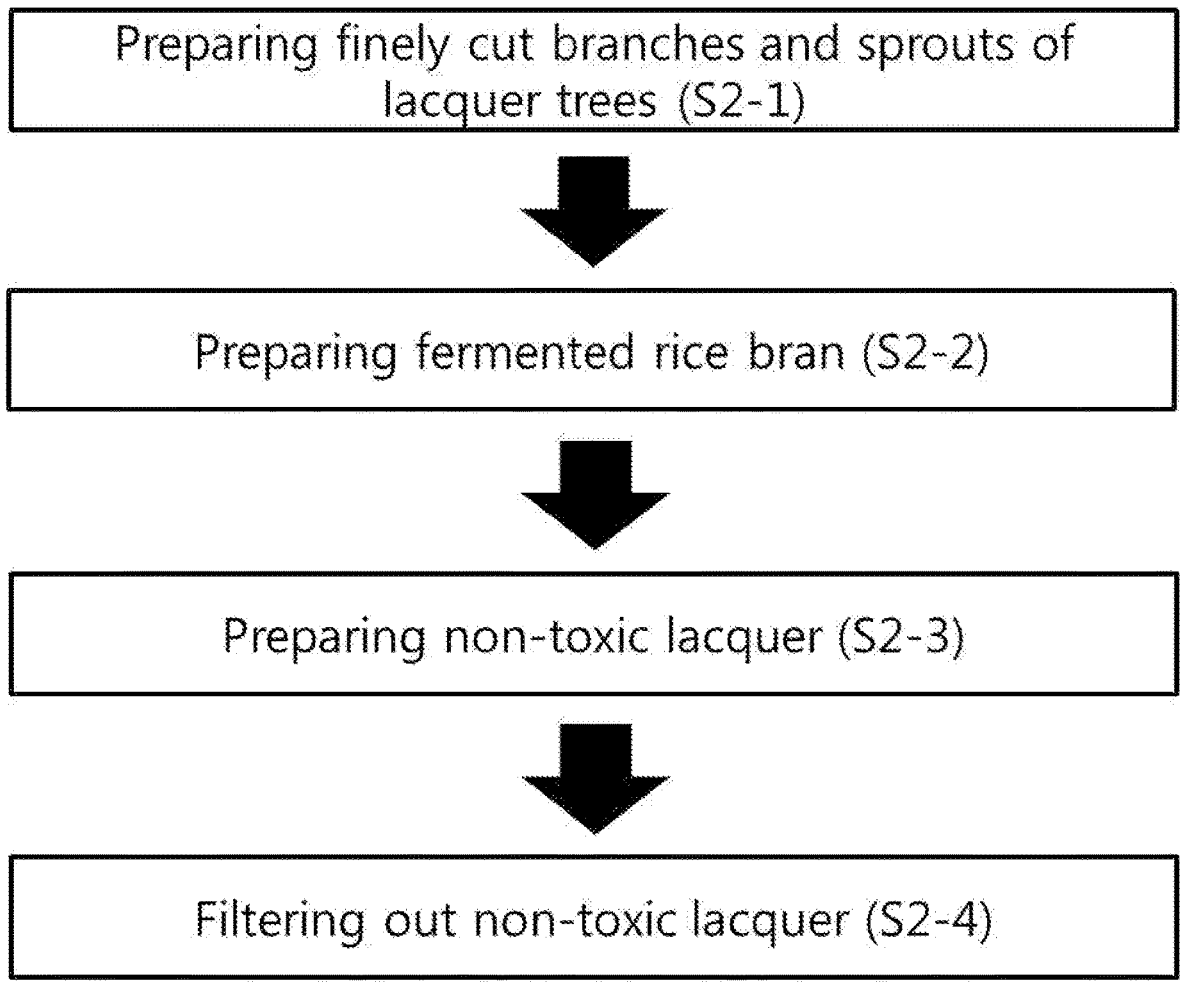
FIG. 2 is a stage flowchart of a method for preparing non-toxic lacquer using branches and sprouts of lacquer trees in accordance with an aspect of the present invention.

FIG. 2 is a stage flowchart of a method for preparing non-toxic lacquer using branches and sprouts of lacquer trees in accordance with an aspect of the present invention.

The method for preparing non-toxic lacquer using branches and sprouts of lacquer trees in accordance with an aspect of the present invention comprises:

after cleaning and drying the sprouts of the lacquer trees, finely cutting the sprouts of the lacquer trees in 1 cm to 2 cm lengths to prepare the finely cut sprouts of the lacquer trees (S2-1); preparing the fermented rice bran (S2-2); and after putting and sealing the finely cut branches and sprouts of the lacquer trees, the fermented rice bran and sugar in the pottery, ripening them at a temperature in the range of 15° C. to 20° C. for 3 months or more to prepare the non-toxic lacquer (S2-3).

Firstly, the step (S2-1) of preparing the finely cut branches and sprouts of the lacquer trees is a process that after cleaning the branches and sprouts of the lacquer trees and drying them to the extent of removing moisture, the branches and sprouts of the lacquer trees are finely cut in 1 cm to 2 cm lengths to prepare the finely cut branches and sprouts of the lacquer trees.

Next, the step (S2-2) of preparing the fermented rice bran was explained above, and thus, the repetitive explanation thereof will be avoided.

Next, the step (S2-3) of preparing the non-toxic lacquer is a process that after mixing and putting the finely cut branches and sprouts of the lacquer trees in the step (S2-1) and the fermented rice bran and the sugar prepared in the step (S2-2) in the pottery, and sealing the pottery by covering its opening by the cotton cloth and the like, they are fermented and ripened at a temperature in the range of 15 t to 20° C. for 3 months or more, preferably, for 3 to 4 months, thereby preparing the non-toxic lacquer.

The fermented rice bran used in the step (S2-3) of preparing the non-toxic lacquer in accordance with an aspect of the present invention was explained above, and thus, the repetitive explanation thereof will be avoided.

In the step (S2-3), more sugar is used unlike the step (S1-4), but this is another aspect of a method for removing the toxicity of lacquer.

For the reaction of detoxification of lacquer, the mixing at the rate of 10 to 15 parts by weight of the fermented rice bran and 25 to 30 parts by weight of the sugar, with respect to 100 parts by weight of the finely cut branches and stems of the lacquer trees, is preferable. This results in the problem that when using the sugar at a content of less than 25 parts by weight and more than 30 parts by weight, the detoxification of the lacquer is weakened.

Because the limited inflow of oxygen is needed for proceeding with the smooth detoxification reaction, it is preferable to cover and seal the opening of the container using the cotton cloth and the like.

A fermenting and ripening temperature is preferably from 15° C. to 20° C., and if it is less than 15° C., the fermentation is weakened to make it difficult to proceed with the detoxification, and if it is more than 20° C., the fermentation velocity is excessive, such that toxicity may be left locally.

Additionally, by implementing the step (S2-4) of filtering out the fermented lacquer using the cotton cloth or gauze, the pure non-toxic lacquer from which the impurities of the branches and stems of the lacquer trees are removed can be obtained. The non-toxic lacquer from which the impurities are removed is diluted with the drinking water and thus, the non-toxic lacquer diluted in the drinking water can be conveniently drunk.

It is assumed that only toxicity of urushiol is selectively removed, which can be disproved because a skin rash, pain or the like is not reported.

The method for preparing the non-toxic lacquer in accordance with an aspect of the present invention has an advantageous effect capable of detoxifying all of tender sprouts of the lacquer trees as well as thick and rough branches and/or stems of the lacquer trees.

In accordance with the method for preparing the non-toxic lacquer according to an aspect of the present invention, while detoxifying urushiol as toxicity of lacquer trees by using a nature-friendly method without any high treatment, the non-toxic lacquer in which 100 natural pharmaceutical ingredients (fucidin, sulurretin, etc.) contained in the lacquer is entirely preserved can be prepared.

Hereinafter, the other aspects of the present invention which manufactures a variety of detoxified lacquer fermentation grain foods such as the fermented rice bran (coenzyme), the powder made of dried grains, and the grain nutrient food by using the non-toxic lacquer prepared in accordance with an aspect of the present invention will be explained.

Figure 3:
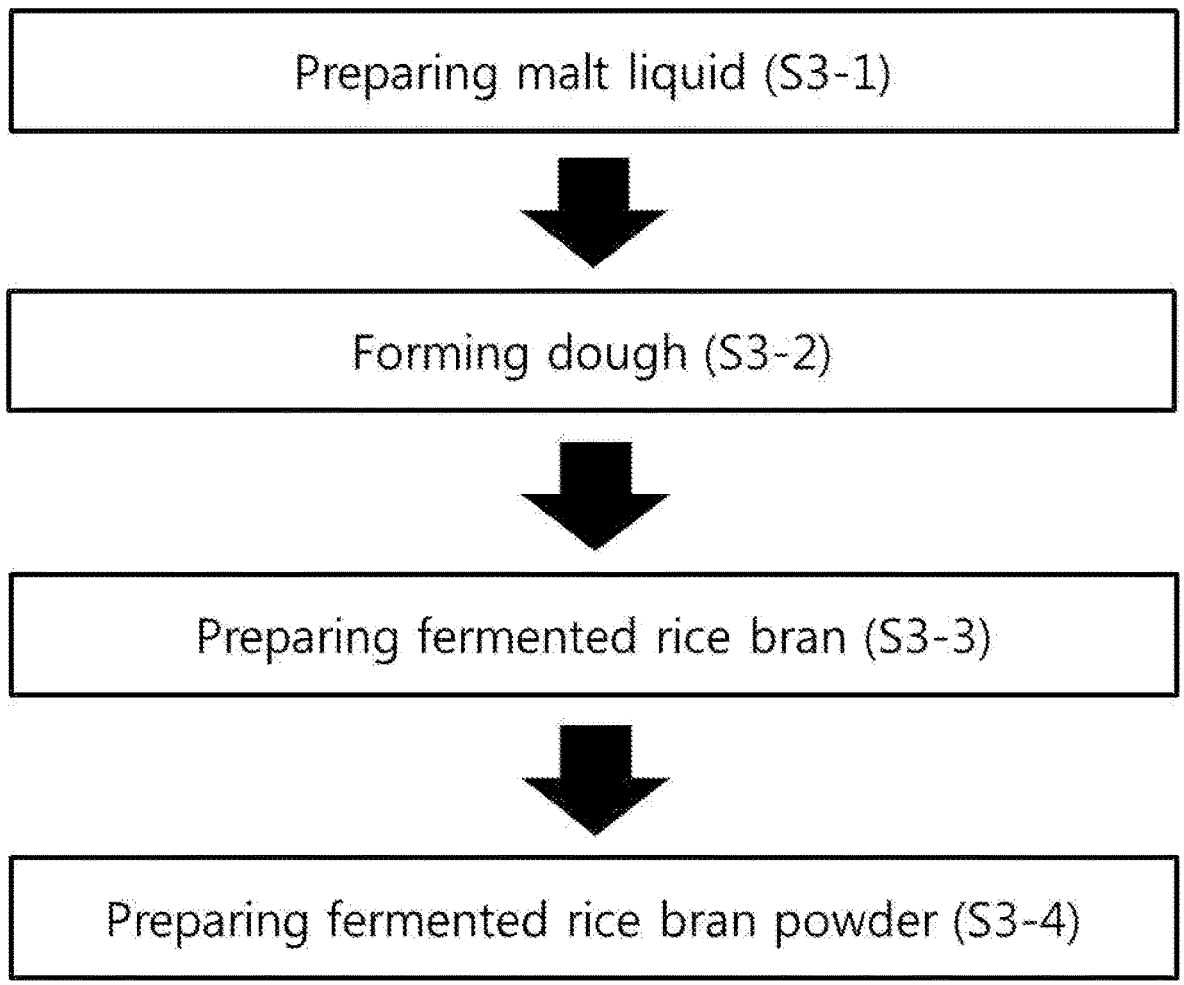
FIG. 3 is a stage flowchart of a method for manufacturing fermented rice bran powder using the prepared non-toxic lacquer in accordance with another aspect of the present invention.

FIG. 3 is a stage flowchart of a method for manufacturing fermented rice bran powder using the prepared non-toxic lacquer in accordance with another aspect of the present invention.

The method for manufacturing the fermented rice bran powder in accordance with another aspect of the present invention comprises:

preparing a malt liquid in which malt brews by putting the malt in the drinking water for 10 hours or more (S3-1); forming dough by mixing a polished rice bran (米糠) powder, the malt liquid and the prepared non-toxic lacquer in accordance with the method (S3-2); putting the formed dough in the plastic bag and thinly stretching and sealing the formed dough, and thereafter fermenting a same at a temperature in the range of 40° C. to 45° C. for 4 days or more to prepare a fermented rice bran (S3-3); and drying the fermented rice bran at 45° C. or less, and thereafter grinding a same to prepare the fermented rice bran powder (S3-4).

First, the step (S3-1) of preparing the malt liquid was explained above, and thus, the repetitive explanation thereof will be avoided.

Next, the step (S3-2) of forming the dough is a process of forming the dough by mixing the polished rice bran (米糠) powder, the malt liquid and the non-toxic lacquer.

Rice bran (米糠) is a byproduct created after brown rice is polished to white rice, and is called rice bran, and is rich in all kinds of vitamins (specifically, $B_1$ and $B_6$), minerals and fiber. The rice bran as a byproduct of rice was excluded from how we eat, in terms of a sanitary problem that it is high in unsaturated fats and is thus acidified quickly, and a nourishing viewpoint of dropping an absorption rate when taking in the rice bran intactly. However, these days, as the rice bran was subjected to heat treatment, there was an attempt to eat the rice bran. In contrast, the present invention chooses a method in which the rice bran is fermented and eaten, and in the process, the rice bran becomes live enzyme with increased amounts of $\gamma$-oryzanol, GABA, tocotrienol, octacosanol, phytic acid, linolenic acid, saponin and so forth.

A diastatic enzyme such as amylase and so forth, contained in the malt, proceeds with fermentation of the rice bran.

However, since the rice bran is high in unsaturated fats and is thus acidified easily. Thus, in order to extend a retention period and increase enzyme activity by blocking the acidification, the acidification needs to be prevented using the prepared non-toxic lacquer in accordance with an aspect of the present invention.

For improvement of preservation through acidification prevention, it is preferable to mix 40 to 45 parts by weight of the malt liquid and 10 to 15 parts by weight of the prepared non-toxic lacquer in accordance with an aspect of the present invention, with regard to 100 parts by weight of the rice bran powder, preferably, within one week after the polishing.

The malt liquid and the non-toxic lacquer are poured in the polished rice bran powder, and they are mixed to form dough.

Next, the step (S3-3) of preparing the fermented rice bran is a process that after the formed dough is put in the plastic bag and is thinly stretched and sealed, it is fermented at a temperature in the range of 40° C. to 45° C. for 4 days or more to prepare the fermented rice bran.

The formed dough is put in the plastic bag such as a zipperbag and is stretched such that the rice bran can be uniformly fermented on the whole, and then, its zipper is closed to seal the plastic bag. If the sealed plastic bag is preserved to maintain a temperature of 40° C. to 45° C. for 4 days or more, preferably, for 4 days to 6 days, the fermentation of the rice bran proceeds sufficiently.

Lastly, the step (S3-4) of preparing the fermented rice bran powder is a process that the fermented rice bran is dried at a temperature of 45° C. or less and is then grinded to prepare the fermented rice bran powder. If the fermented rice bran is dried at a temperature of more than 45° C., the activity of the live enzyme may be lowered or lost, which requires attention. The dry period may vary based on seasons and weather (humidity), and usually takes 4 to 5 days.

Figure 4:
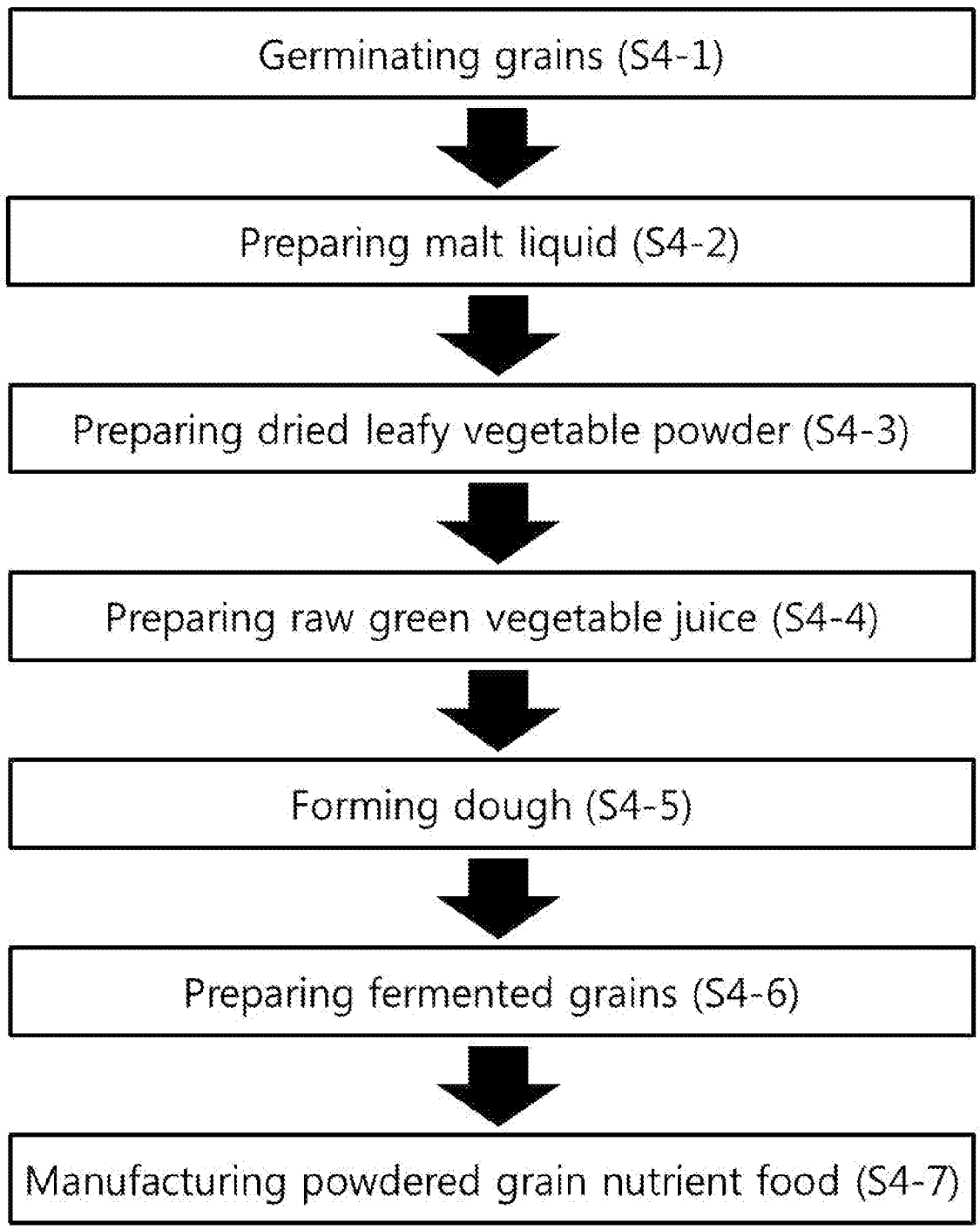
FIG. 4 is a stage flowchart of a method for manufacturing a powdered grain nutrient food using the prepared non-toxic lacquer in accordance with another aspect of the present invention.

FIG. 4 is a stage flowchart of a method for manufacturing a fermented powdered grain nutrient food using the prepared non-toxic lacquer in accordance with another aspect of the present invention.

The method for manufacturing the powered grain food in accordance with another aspect of the present invention comprises:

immersing or wet-spraying one of grains consisting of rice, barley, barn grass, beans, millet and adlay, or at least five grains using drinking water in which the lacquer prepared in accordance with any one of claims 1 to 4 is contained at a content of 0.2 wt % to 0.5 wt %, thereby germinating grains (S4-1); preparing a malt liquid in which malt brews by putting the malt in the drinking water for 10 hours or more (S4-2); preparing a fermented rice bran (S4-3); preparing raw green vegetable juice by grinding fresh vegetables varying according to seasons regarding raw vegetables (S4-4); forming dough by mixing the germinated grains, the malt liquid, dried leafy vegetable powder, the raw green vegetable juice and the lacquer prepared according to the method (S4-5); after putting the formed dough in the plastic bag and thinly stretching and sealing the formed dough, fermenting a same at a temperature in the range of 40° C. to 45° C. for 4 days or more to prepare fermented grains (S4-6); and preparing the powered grain food by drying and grinding the fermented grains at 45° C. or less (S4-7).

Firstly, the step (S4-1) of germinating grains is a process of germinating the grains by immersing the grains in the drinking water in which the lacquer prepared according to an aspect of the present invention is contained at a content of 0.2 wt % to 0.5 wt %, or wet-spraying the grains in the drinking water in which the lacquer prepared according to an aspect of the present invention is contained at a content of 0.2 wt % to 0.5 wt %.

The grains used in the present invention can be used alone or by mixture by selecting any one of rice (e.g.: brown rice, brown glutinous rice and sorghum glutinous rice), barley (e.g.: glutinous barley), barn grass, beans (e.g.: a kind of small bean, black soybeans, red beans and mung beans), millet and adlay, or at least five grains.

If the grains are immersed in the drinking water in which the prepared non-toxic lacquer in accordance with an aspect of the present invention is contained at a content of 0.2 wt % to 0.5 wt %, for example, while the drinking water is replaced three times or more each day, the grains are immersed for 5 days or more and can be germinated. In contrast, even if the drinking water in which the non-toxic lacquer is contained at a content of 0.2 wt % to 0.5 wt %, is wetted (watered) and sprayed regularly, the grains can be germinated.

Water needs to be supplied continuously to germinate the grains. However, when the grains are immersed in the drinking water for days, the grains are deteriorated, and accordingly, the drinking water needs to be frequently replaced. The present invention has an advantageous effect of blocking deterioration of the grains and shortening germination time because the grains are immersed using the drinking water in which the non-toxic lacquer prepared in accordance with an aspect of the present invention is contained at a content of 0.2 wt % to 0.5 wt %. If the non-toxic lacquer is used at a content of less than 0.2 wt %, the deterioration prevention effect are lessened, and if the non-toxic lacquer is used at a content of more than 0.5 wt %, the germination of the grains may be more delayed.

Next, the step (S4-2) of preparing the malt liquid was explained above, and thus, the repetitive explanation thereof will be avoided.

In addition, the step (S4-3) of preparing the fermented rice bran was explained above, and thus, the repetitive explanation thereof will be avoided.

Next, the step (S4-4) of preparing raw green vegetable juice is to supplement poor nutrition of the grains by using, as dough water, juice obtained by grinding fresh vegetables varying according to seasons with raw vegetables contained in natural bioactive substances instead of the drinking water. As the vegetables used in the present invention is cultivated or grown outdoors, edible plants such as edible plants, wild grasses and so forth, are acceptable. However, it is preferable to choose and use materials of which the effectiveness was already proved.

Next, the step (S4-5) of forming the dough is a process of mixing the germinated grains, the malt liquid, the fermented rice bran, the raw green vegetable juice and the non-toxic lacquer, wherein amylase contained in the malt and the fermented rice bran proceed with the fermentation of the germinated grains. However, since gemmules of the grains are high in unsaturated fats, they are easily acidified. Thus, the acidification needs to be prevented using the prepared non-toxic lacquer in accordance with an aspect of the present invention in order to extend a retention period and increase enzyme activity by blocking the acidification.

For improvement of the fermenting efficiency and the retention period of the powdered grain food in the form of powder made of dried grains, it is preferable to mix 10 to 15 parts by weight of the malt liquid, 25 to 35 parts by weight of the fermented rice bran, 40 to 55 parts by weight of the raw green vegetable juice, and 10 to 15 parts by weight of the lacquer prepared according to the method, with regard to 100 parts by weight of the germinated grains.

100 parts by weight of the germinated grains, 10 to 15 parts by weight of the malt liquid, 25 to 35 parts by weight of the fermented rice bran, 40 to 55 parts by weight of the raw green vegetable juice, and 10 to 15 parts by weight of the non-toxic lacquer are poured and thoroughly mixed to form dough, thereby manufacturing the powder made of dried grains.

A powered grain food having a nourishing form as another embodiment different from the form of powder made of dried grains can be manufactured. However, in this case, the method may further comprise: choosing and preparing at least five grains; preparing the dried leafy vegetable powder by drying and grinding any one of marine algae, fruits or mushrooms; and preparing a fermented broth using any one of medical herbs, wild herbs and vegetables, and fruits, and the method may be achieved in the process of forming the dough by mixing the malt, the fermented rice bran and the raw green vegetable juice in the step (S4-5') of forming the dough.

In this case, for improvement of the fermenting efficiency and the retention period of the powdered grain food in the nourishing form, it is preferable to further mix 10 to 15 parts by weight of the malt liquid, 25 to 30 parts by weight of the fermented rice bran, 40 to 55 parts by weight of the raw green vegetable juice, and 10 to 15 parts by weight of the lacquer prepared according to the method, 5 to 10 parts by weight of the dried leafy vegetable powder and 15 to 20 parts by weight of the fermented broth, with regard to 100 parts by weight of the germinated grains.

Next, the step (S4-6) of preparing the fermented grains is a process that after the formed dough is put in the plastic bag and is thinly stretched and sealed, at a temperature in the range of 40° C. to 45° C., the powder made of dried grains is fermented for 4 days or more, and the powered grain food having a nourishing form is fermented for 6 days or more, thereby preparing the fermented grains.

The formed dough is put in the plastic bag such as a zipperbag and is thinly stretched such that the grains can be uniformly fermented on the whole, and then, its zipper is closed to seal the plastic bag. The sealed plastic bag is managed to maintain a temperature of 40° C. to 45° C. for 5 to 6 days or more, such that the fermentation of the grains proceeds sufficiently.

Lastly, the step (S4-7) of preparing the dried leafy vegetable powder and the powered grain food having the nourishing form is a process that after the fermented grains are dried at a temperature of 40° C. to 45° C. or less, they are grinded.

If the fermented grains are pulverized, they are mixed with water instead of rice and can be drunk. Thus, it is not necessary to dry and grind the fermented grains. If the fermented grains are dried at a temperature of more than 40° C., the activity of the live enzyme may be lowered or lost, which requires attention. The dry period may vary based on seasons and weather (humidity), and usually takes 5 to 6 days.

Conventional powder made of dried grains is made by roasting or steaming grains to pulverize the roasted or steamed grains, and has a problem that when having the powder, people with a bad digestion or a weak stomach have acid reflux or a bit of sour vomit. However, the powder made of dried grains manufactured in accordance with another of the present invention has an advantage that the people can take in or drink it without this problem and the retention period can be improved.

The present invention can be more clearly understood through the following embodiments, the following examples are for the purpose of exemplarily explaining the present invention, and the protection scope limited by the claims attached hereto do not intend to be limited.

Example

Example 1: Manufacture of the Non-Toxic Lacquer Using the Stems of Lacquer Trees The stems of the lacquer trees are cut and split in 5 cm lengths, and then, the cut stems of the lacquer trees are cleaned and dried to prepare 3000 g of the stems of the lacquer trees. 100 g of the malt is put in 1700 g of the drinking water for 11 hours to obtain a yellowish malt liquid. 1750 g of the malt liquid and 800 g of the fermented rice bran are put in the pottery, and its opening is sealed by the cotton cloth and the pottery is covered with a lid, and thereafter, the pottery is maintained at a temperature of 20° C. to 25° C. and is simultaneously fermented for 72 hours to obtain 1300 g of the fermented malt juice. 3300 g of the drinking water, 3000 g of the finely cut stems of the lacquer trees and 1300 g of the fermented malt juice are put in the pottery, and its opening is sealed by the cotton cloth and covered with the lid, and thereafter, the pottery is maintained at a temperature of 10° C. to 20° C. and is simultaneously fermented for 5 months, the cotton cloth is spread on the basket, and the impurities of the stems of the lacquer trees, the fermented bran rice and so forth, are filtered out to obtain 2500 g of light brown non-toxic lacquer.

Example 2: Manufacture of the Non-Toxic Lacquer Using the Branches and Sprouts of Lacquer Trees The branches and sprouts of the lacquer trees are cleaned to remove its moisture, and they are cut in 2 cm lengths to prepare 3000 g of the branches and sprouts of the lacquer trees. 3000 g of the finely cut branches and sprouts of the lacquer trees, 200 g of the fermented rice bran and 1100 g of sugar are put in the pottery, and its opening is sealed by the cotton cloth and covered with the lid, and thereafter, the pottery is maintained at a temperature of 15° C. to 20° C. and is simultaneously fermented for 3 months, and the cotton cloth is spread on the basket, and the impurities of the branches and stems of the lacquer trees, the fermented bran rice and so forth are filtered out to obtain 700 g of dark brown non-toxic lacquer.

Example 3: Manufacture of the Fermented Rice Bran Enzyme Using the Non-Toxic Lacquer 25 g of the malt is put in 200 g of the drinking water for 11 hours to obtain 215 g of a yellowish malt liquid. 215 g of the malt liquid and 60 g of the non-toxic lacquer obtained from Example 1 are put in 500 g of rice bran powder within one week after the milling, and they are mixed to form dough. The formed dough is divided and widely put in zipperbags, and the zipperbag are zipped and sealed, and thereafter, the dough is fermented at a temperature of 40° C. to 45° C. for 5 days to obtain the fermented rice bran. The fermented rice bran is dried at a temperature of 30° C. to 40° C. for 4 days and is then grinded to obtain fermented rice bran enzyme powder.

Example 4: Manufacture of the Grain Nutrient Food Using the Non-Toxic Lacquer

The grains are immersed in the drinking water in which the prepared non-toxic lacquer according to Example 1 is contained at a content of 0.5 wt %, and the drinking water is replaced three times each day, thereby fermenting brow rice on the fourth day. 50 g of the malt is put in 300 g of the drinking water for 11 hours to obtain 330 g of the yellowish malt liquid. Marine algae, fruits, mushrooms and so forth are dried and grinded to prepare 100 g of dried leafy vegetable powder. Celery, water parsley, edible aster, paprika, cabbages, onions, carrots and so forth, are grinded to prepare 500 g of green vegetable juice. 300 g of the fermented rice bran obtained from Example 3 is prepared. Medical herbs, wild herbs and fruits are seasoned with sugar to prepare 200 g of ripened and fermented broth. In 1100 g of the germinated grains, 330 g of the malt liquid, 100 g of the dried leafy vegetable powder, 500 g of the raw green vegetable juice, and 150 g of the non-toxic liquid and 200 g of the fermented broth obtained from Example 1 are uniformly mixed to form the dough. The formed dough is divided and widely put in zipperbags, and the zipperbags are zipped and sealed, and thereafter, the dough is fermented at a temperature of 40° C. to 45° C. for 5 days to obtain the fermented grains. The fermented grains are dried at a temperature of 35° C. to 38° C. for 5 days and are then grinded to obtain grain nutrient food powder.

Examples

Experimental Example 1: Experiment of Confirming the Toxicity of the Lacquer

The lacquer prepared according to Example 1 is diluted at contents of 2 wt %, 4 wt % and 6 wt %, respectively, in the drinking water, and thereafter, their contents are gradually increased at 10 day intervals over the first, second and third times, thereby requesting 30 subjects sensitive to the lacquer to take in the lacquer.

As a comparative example, it is excluded that the malt juice and the fermented rice bran are not used, and the lacquer prepared in the same method as Example 1 is diluted at contents of 2 wt %, 4 wt % and 6 wt %, respectively, in the drinking water, and thereafter, their contents are gradually increased at 10 day intervals over the first, second and third times, thereby requesting the same 30 subjects to take in the lacquer.

The result is shown in [Table 1].

TABLE 1

| Examples | Drinking Water/Lacquer (wt %) | Painful (Rash) Area | Pain Intensity | Conscious Frequency (/日) |
|---|---|---|---|---|
| Experimental Example 1 | 2 | None | 0 | None |
| Experimental Example 2 | 4 | None | 0 | None |
| Experimental Example 3 | 6 | None | 0 | None |
| Comparative Example 1 | 2 | Anus | 0.2 | At least one time |
| Comparative Example 2 | 4 | Anus and Neck | 0.5 | At least three times |
| Comparative Example 3 | 6 | Anus, Neck and Face | 1 | At least five times |

With regard to the pain intensity, a skin rash degree is indicated using 0 (weakness) to 10 (strength).

The conscious frequency indicates how many times the subjects have itching per day.

With reference to [Table 1], it can be confirmed that the toxicity caused by the lacquer was substantially removed from the lacquer in accordance with Example 1 prepared using the malt liquid and the fermented rice bran.

Experimental Example 2: Experiment of the Retention Period of the Grain Nutrient Food The grain nutrient food powder prepared according to Example 4 using the lacquer prepared according to Example 1 (Experimental Example 4), and the grain nutrient food powder prepared according to Example 4 by not using the lacquer prepared according to Example 1 (Comparative Example 4) are slowly cooled and stored at a temperature of really 10° C. or less, and whether to grow mold is simultaneously observed with the naked eye. The result therefrom is summarized as shown in [Table 2].

TABLE 2

| Example | Observation Time of First Mold |
|---|---|
| Comparative Example 4 | The sixty-second day |
| Experimental Example 4 | The one hundred and twenty-ninth day |

As shown in [Table 2], the preservation of the grain nutrient food powder is about two times improved by the detoxified lacquer prepared in accordance with the present invention.

Experimental Example 3: Experiment of brown rice germination using the non-toxic lacquer

TABLE 3

| | Germination Period | | Germination |
|---|---|---|---|
| | Summer | Winter | Percent (%) |
| Experimental Example 5 | 5 days | 6 days | 96 |
| Comparative Example 5 | 6 days | 8 days | 72 |

With reference to [Table 3], it can be confirmed that if the grains are germinated in the drinking water in which the prepared non-toxic lacquer in accordance with the present invention is contained at a content of 0.5 wt % (Experimental Example 5), the germination period is declined by one day or more (20% or more), and the germination percent is enhanced by 24% because of the pharmaceutical activity of the detoxified lacquer, as compared to the germination using only the drinking water (Comparative Example 5).

Experimental Example 4: Experiment of Preferences of the Grain Nutrient Food

Each 10 men and women in their 20s and 30s, 40s and 50s, and 60s and 70s, i.e., a total of 60 people, were requested to take in the prepared grain nutrient powder in accordance with Example 4 (Experimental Example 6), and on the next day, they were requested to take in the grain nutrient powder prepared by not using the lacquer in accordance with the present invention unlike Example 4 (Comparative Example 6). Thereafter, average values of evaluating the preferences on the basis of 100 points are summarized as shown in [Table 4].

TABLE 4

| Example | 20s and 30s | 40s and 50s | 60s and 70s | Whole Average Value |
|---|---|---|---|---|
| Experimental Example 6 | 91 | 94 | 98 | 94.3 |
| Comparative Example 6 | 83 | 85 | 86 | 84.7 |

The grain nutrient food of Experimental Example 6 is more preferred than the grain nutrient food of Comparative Example 6 (8 to 12 points) at all ages, and specifically, in the elderly purpose (60s and 70s), the grain nutrient food of Experimental Example 6 is more preferred. It is recognized on a survey that this is because there are almost no side effects that the elderly with a bad digestion or a weak stomach have acid reflux or a bit of sour vomit.

In the above mentioned disclosure, the present invention has been shown and explained using specific preferable examples, but it would be obvious to a person having ordinary skill in the art to which the invention pertains that the present invention can be variously remodeled and changed within a limit which does not make a breakaway from a technical feature or field of the present invention arranged by the claims attached hereto.

What is claimed is:
1. A method for preparing a non-toxic lacquer composition, the method comprising:
cutting and splitting stems of lacquer trees in 4 cm to 6 cm lengths, cleaning and drying them to prepare the cut and split stems of the lacquer trees;
preparing a malt liquid in which malt is brewed by putting the malt in water and brewing for 10 hours;

putting and sealing the prepared malt liquid and a fermented rice bran in a pottery container and fermenting at a temperature in the range of 20° C. to 25° C. for 70 to 80 hours to prepare a fermented malt juice; and putting the cut and split stems of the lacquer trees, water and the fermented malt juice in the container, covering and sealing the container, and thereafter ripening the contents at a temperature in the range of 10° C. to 20° C. for 5 months to prepare the non-toxic lacquer composition.

2. The method according to claim 1, wherein 40 to 50 parts by weight of the fermented rice bran with regard to 100 parts by weight of the prepared malt liquid is added in the pottery container for preparing the fermented malt juice, and wherein 100 to 120 parts by weight of the water and 75 to 85 parts by weight of the fermented malt juice with regard to 100 parts by weight of the cut and split stems of the lacquer trees, are put in the pottery container for preparing the non-toxic lacquer composition.

3. A method for manufacturing fermented rice bran powder, the method comprising:

preparing a malt liquid in which malt is brewed by putting the malt in water and brewing for 10 hours;

mixing a polished rice bran powder and the malt liquid with the prepared non-toxic lacquer composition according to claim 1 to form dough;

putting the formed dough in a plastic bag, stretching and sealing the formed dough, and thereafter fermenting the dough at a temperature in the range of 40° C. to 45° C. for 4 days to prepare a fermented rice bran; and drying the fermented rice bran at 45° C. and thereafter grinding it to prepare the fermented rice bran powder.

4. The method according to claim 3, wherein in the step of forming the dough, 35 to 40 parts by weight of the malt liquid with regard to 100 parts by weight of the polished rice bran powder is mixed with 10 to 15 parts by weight of the prepared non-toxic lacquer composition.

5. A method for manufacturing a powdered grain food, the method comprising:

immersing or wet-spraying at least one of grains selected from the group consisting of rice, barley, barn grass, beans, millet and adlay with water comprising the non-toxic lacquer composition prepared according to claim 1 at an amount of 0.2 wt % to 0.5 wt %, thereby germinating the grains;

preparing a malt liquid in which malt is brewed by putting the malt in the water and brewing for 10 hours;

preparing dried leafy vegetable powder by drying and grinding any one of marine algae, beans or mushrooms;

preparing a fermented broth obtained by fermenting and ripening any one of medical herbs, wild herbs and vegetables, or fruits;

preparing raw green vegetable juice by grinding raw green vegetables;

forming dough by mixing the germinated grains, a fermented rice bran, the malt liquid, the fermented broth, the dried leafy vegetable powder, the raw green vegetable juice and the non-toxic lacquer composition;

putting the formed dough in a plastic bag, stretching and sealing the formed dough, and thereafter fermenting the dough at a temperature in the range of 40° C. to 45° C. for 4 days, thereby preparing fermented grains; and drying the fermented grains at 40° C. and thereafter grinding the dried fermented grains to prepare the powdered grain food.

6. The method according to claim 5, wherein in the step of forming the dough, 25 to 35 parts by weight of the fermented rice bran, 15 to 20 parts by weight of the fermented broth, 5 to 10 parts by weight of the dried leafy vegetable powder, 40 to 45 parts by weight of the raw green vegetable juice and 10 to 15 parts by weight of the non-toxic lacquer composition, with regard to 100 parts by weight of the germinated grains, are mixed.

\* \* \* \* \*